United States Patent [19]

Tice et al.

[11] Patent Number: 4,530,840
[45] Date of Patent: Jul. 23, 1985

[54] INJECTABLE, LONG-ACTING MICROPARTICLE FORMULATION FOR THE DELIVERY OF ANTI-INFLAMMATORY AGENTS

[75] Inventors: Thomas R. Tice, Birmingham; Danny H. Lewis, Gardendale; Donald R. Cowsar; Lee R. Beck, both of Birmingham, all of Ala.

[73] Assignees: The Stolle Research and Development Corporation, Cincinnati, Ohio; Southern Research Institute, Birmingham, Ala.

[21] Appl. No.: 402,857

[22] Filed: Jul. 29, 1982

[51] Int. Cl.³ .............................................. A61K 31/58
[52] U.S. Cl. ...................................... 514/179; 514/180
[58] Field of Search ................ 424/238, 241, 243, 31, 424/32

[56] References Cited

U.S. PATENT DOCUMENTS

| | | | |
|---|---|---|---|
| 4,066,747 | 1/1978 | Capozza | 424/238 |
| 4,196,188 | 4/1980 | Besins et al. | 424/238 |
| 4,267,173 | 5/1981 | Draper et al. | 424/243 |
| 4,328,204 | 5/1982 | Wasserman et al. | 424/238 |
| 4,374,121 | 2/1983 | Cioca | 424/238 |
| 4,389,330 | 6/1983 | Tice et al. | 427/213.36 |

Primary Examiner—Elbert L. Roberts
Attorney, Agent, or Firm—Oblon, Fisher, Spivak, McClelland & Maier

[57] ABSTRACT

An anti-inflammatory agent containing microparticle composition prepared by a process, comprising (a) dissolving or dispersing an anti-inflammatory agent in a solvent and dissolving a biocompatible and biodegradable wall forming material in said solvent; (b) dispersing said solvent containing said anti-inflammatory agent and wall forming material in a continuous phase processing medium; (c) evaporating a portion of said solvent from said dispersion of step (b), thereby forming microparticles containing said anti-inflammatory agent in the suspension; and (d) extracting the remainder of the solvent from said microcapsules.

12 Claims, 1 Drawing Figure

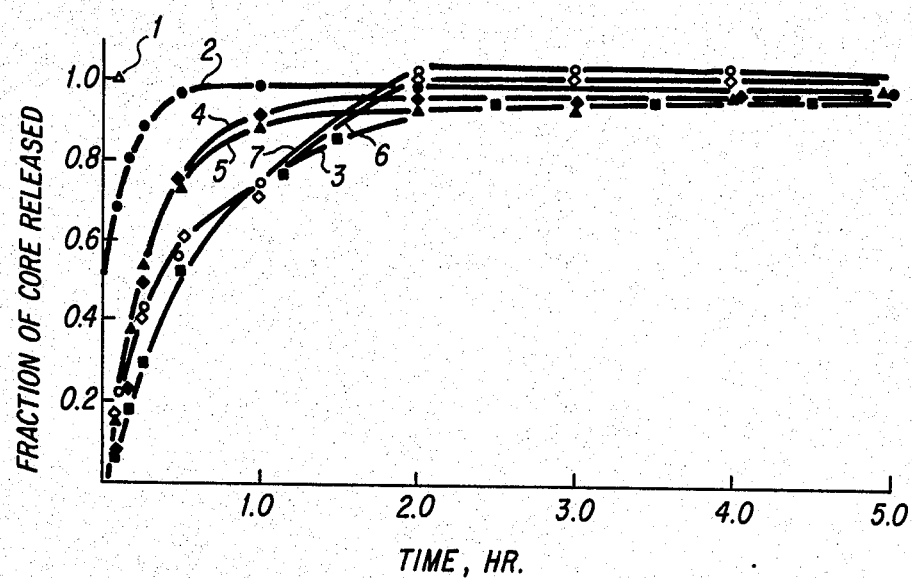

INJECTABLE, LONG-ACTING MICROPARTICLE FORMULATION FOR THE DELIVERY OF ANTI-INFLAMMATORY AGENTS

BACKGROUND OF THE INVENTION

Field of the Invention

The present invention relates to a method of treating inflammation, particularly of the joints with a long-acting, slow release anti-inflammatory agent containing composition.

Description of the Prior Art

Inflammations of the various joints of the body are quite frequently manifestations of a disease such as rheumatoid arthritis or osteoarthritis. In the treatment of the inflammation, an anti-inflammatory agent in injectable form is administered by intra-articular injection directly into the joint or joints which exhibit inflammation. Normally, for intra-articular injection an aqueous suspension of an anti-inflammatory agent such as a corticosteroid is injected directly into a joint. On the other hand, for the treatment of a variety of diseases and disorders such as endocrine disorders, rheumatic disorders, collagen diseases, dermatologic diseases and other diseases and disorders involving inflammation, an anti-inflammatory agent is commonly administered systemically by oral preparations containing the anti-inflammatory agent. When oral therapy is not feasible, the anti-inflammatory agent can be administered by intra-muscular injection. In many cases it is highly desirable to be able to administer anti-inflammatory agents, particularly to skeletal joints, in a form which retains the drug at the site administered and which slowly releases the drug so that a long acting anti-inflammatory effect is achieved. An example of an anti-inflammatory agent containing composition which can be directly administered by intra-articular injection is cortisol palmitate microencapsulated in a lipsome wall forming material as disclosed by de Silva et al, *The Lancet*, pp. 1320–22 (1979). However, a need continues to exist for a microparticle formulation which contains an anti-inflammatory agent of improved slow release, long acting characteristics.

SUMMARY OF THE INVENTION

Accordingly, one object of the present invention is to provide a way of conveniently administering anti-inflammatory agents to the body in a formulation which is long-acting, preferably for a period greater than one month.

Another object of the invention is to provide a formulation containing an anti-inflammatory agent which is injectable into inflamed joints and that remains in the joints after injection to achieve a local delivery of the active agent.

Briefly, these objects and other objects of the present invention as hereinafter will become more readily apparent can be attained by an anti-inflammatory agent containing microparticle composition comprising: (a) dissolving or dispersing an anti-inflammatory agent in a solvent and dissolving a biocompatible and biodegradable wall forming material in said solvent; (b) dispersing said solvent containing said anti-inflammatory agent and wall forming material in a continuous phase processing medium; (c) evaporating a portion of said solvent from said dispersion of step (b), thereby forming microparticles containing said anti-inflammatory agent in the suspension; and (d) extracting the remainder of the solvent from said microcapsules.

BRIEF DESCRIPTION OF THE DRAWING

A more complete appreciation of the invention and many of the attendant advantages thereof will be readily obtained as the same becomes between understood by reference to the following detailed description when considered in connection with the accompanying drawing, wherein:

The Figure shows the IN VITRO release profiles of five methylprednisolone containing microparticles and two unencapsulated samples of methylprednisolone acetate.

DETAILED DESCRIPTION OF THE PREFERRED EMBODIMENTS

The present invention is directed to an injectable, long-acting microparticle formulation which contains an anti-inflammatory compound for administration at the sites of inflammation in the body. Suitable anti-inflammatory compounds include enzymes, hormones, phenylbutazones, salicylates, steroids, sulfonamides and the like. A preferred group of materials are corticosteroid compounds including prednisolones such as methylprednisolone-t-butyrate and methylprednisolone acetate, triamcinolones such as triamcinolone acetonide and triamcinolone hexacetonide, dexamethasones such as dexamethasone acetate and dexamethasone phosphate and $\beta$-methasones such as $\beta$-methasone phosphate and $\beta$-methasone acetate.

The formulation of the present invention comprises an anti-inflammatory agent dispersed in microparticles of a polymeric matrix material. The amount of anti-inflammatory agent incorporated in the microparticles usually ranges from less than 1 wt. % to as high as 95 wt. %, preferably 1 to 75 wt. %.

The polymeric matrix material of the microparticles of the present invention must be a biocompatible and biodegradable polymeric material. The term biocompatible is defined as a polymeric material which is not toxic to the human body, it is not carcinogenic and it should not induce inflammation in body tissues. The matrix material should be biodegradable in the sense that the polymeric material should degrade by bodily processes to products readily disposable by the body and should not accumulate in the body. The biodegraded products also should be biocompatible with the body in the sense that the polymeric matrix is compatible with the body. Suitable examples of polymeric matrix materials include poly (glycolic acid), poly-d,l-lactic acid, copolymers thereof, copolyoxalates, polycaprolactone, poly (lactic acid-caprolactone), and the like. Suitable polymeric materials also include waxes such as glycerol mono- and distearate.

The molecular weight of the polymeric matrix material is of some importance. The molecular weight should be high enough so that it forms satisfactory polymer coatings, i.e., the polymer should be a good film former. Usually, a satisfactory molecular weight is greater than 10,000 daltons. However, since the properties of the film are also partially dependent on the particular polymeric material being used, it is very difficult to specify an appropriate molecular weight range for all polymers. The molecular weight of a polymer is also important from the point of view that molecular weight influences the biodegradation rate of the polymer. For a diffusional mechanism of drug release, the polymer should remain intact until all of the drug is released from the microparticles and then degrade. The drug can also be released from the microparticles as the polymeric excipient bioerodes. By an appropriate selection of polymeric materials a microparticle formulation can be made such that the resulting microparticles exhibit both diffusional release and biodegradation release properties.

The microparticle product of the present invention can be prepared by any method which is capable of producing microparticles in a size range acceptable for use in an injectable composition. A preferred method of preparation is the two-step method described in copending U.S. patent application Ser. No. 194,127 filed Oct. 6, 1980. In this method the desired anti-inflammatory compound is dissolved or dispersed in an appropriate solvent. To the anti-inflammatory agent containing medium is added the polymeric matrix material in an amount relative to the active ingredient which gives a product of the desired loading of active agent. Optionally, all of the ingredients of the microparticle product can be blended in the solvent medium together. Suitable solvents for the anti-inflammatory compound and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, water and the like. A preferred solvent for the anti-inflammatory agent is a mixture of acetone in methylene chloride containing up to about 10 wt. % acetone.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and most commonly is water although nonaqueous media such as xylene and toluene and synthetic oils and natural oils can be used. Usually, a surfactant is added to the continuous-phase processing medium to prevent the microparticles from agglomerating and to control the size of the solvent microdroplets in the emulsion. A preferred surfactant-dispersing medium combination is a 1 to 10 wt. % poly (vinyl alcohol) in water mixture. The dispersion is formed by mechanical agitation of the mixed materials. An emulsion can also be formed by adding small drops of the active agent-wall forming material solution to the continuous phase processing medium. The temperature during the formation of the emulsion is not especially critical but can influence the size and quality of the microparticles and the solubility of the drug in the continuous phase. Of course, it is desirable to have as little of the drug in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be too high that the stability of the particular active agent being incorporated in the microparticles is adversely affected. Accordingly, the dispersion process can be conducted at any temperature which maintains stable operating conditions, which preferred temperature being about 0° to 37° C., depending upon the drug and excipient selected.

The dispersion which is formed is a stable emulsion and from this dispersion the organic solvent in the microdroplets in the organic solvent immiscible fluid is partially removed in the first step of the solvent removal process. The solvent can easily be removed by common techniques such as heating, the application of a reduced pressure or a combination of both. The temperature employed to evaporate solvent from the microdroplets is not critical, but should not be that high that it degrades the anti-inflammatory agent employed in the preparation of a given microparticle, nor should it be so high as to evaporate solvent at such a rapid rate to cause defects in the wall forming material. Generally, from 10 to 90%, preferably 40 to 60% of the solvent is removed in the first solvent removal step.

After the first stage solvent removal step, the dispersed microparticles in the solvent immiscible fluid medium are isolated from the fluid medium by any convenient means of separation. Thus, for example, the fluid can be decanted from the microparticle or the microparticle suspension can be filtered. Still other, various combinations of separation techniques can be used if desired.

Following the isolation of the microparticles from the continuous-phase processing medium, the remainder of the solvent in the microparticles is removed by extraction. In this second step, the microparticles can be suspended in the same continuous-phase processing medium used in step one, with or without surfactant, or in another liquid. The extraction medium removes the solvent from the microparticles and yet does not dissolve the microparticles. During the extraction, the extraction medium with dissolved solvent must be removed and replaced with fresh extraction medium. This is best done on a continual basis, where the rate of extraction medium replenishment is critical. If the rate is too slow, agent crystals will protrude from the microcapsules or grow in the extraction medium. Obviously, the rate of extraction medium replenishment for a given process is a variable which can easily be determined at the time the process is performed and, therefore, no precise limits for the rate must be predetermined. After the remainder of the solvent has been removed from the microparticles, the microparticles are dried by exposure to air or by other conventional drying techniques such as vacuum drying, drying over a desiccant, or the like. The process of the present invention is very efficient in encapsulating the anti-inflammatory agent since core loadings of up to 80 wt. %, preferably up to 75 wt. % are obtained.

The microparticle product of the present invention is usually made up of particles of a spherical shape although sometimes the microparticles may be irregularly shaped. The microparticles can vary in size, ranging from submicron to millimeter diameters. Preferably, submicron to 250 μm, preferably 200 μm diameters are desirable for pharmaceutical formulations allowing administration of the microparticles with a standard syringe and needle. The microparticle product of the present invention is useful in the treatment of inflammation of the body which arises from diseases and disorders such as endocrine disorders, rheumatic disorders, collagen diseases, dermatologic diseases, allergic states, ophthalmic diseases, gastrointestinal diseases, respiratory diseases, hematologic diseases, neoplastic diseases, edamatous states, disorders of the nervous system, and the like.

The anti-inflammatory agent bearing microparticles of the present invention are obtained and stored as a dry material. Immediately prior to administration to a subject, the microparticles are suspended in an acceptable pharmaceutical liquid vehicle, the suspension is then drawn into a syringe, and then the suspension is injected into the desired portion of the body such as an affected joint.

The amount of anti-inflammatory agent administered to a subject depends on the particular disease or disorder being treated and the type of anti-inflammatory agent being administered. Since the present invention is not at all concerned with a novel anti-inflammatory agent, but rather a unique microparticle formulation involving encapsulated anti-inflammatory agent, one skilled in the art is well aware of the dosages required to treat a particular subject having a particular disorder involving inflammation with a particular anti-inflammatory agent. Commonly, anti-inflammatory agents are administered in microgram to milligram quantities per day. For the treatment of a large joint of the body such as a knee, shoulder or ankle, the amount of a corticosteroid such as methylprednisolone acetate administered ranges from 20 to 80 mg. For a medium size joint such as an elbow or wrist the amount of corti-costeroid ranges from 10 to 40 mg, while for a small joint such as the metacarpophalangeal, interphalangeal, sternoclavicular and acromioclavicular joints, the amount of drug administered ranges from 4 to 10 mg.

Having generally described this invention, a further understanding can be obtained by reference to certain specific examples which are provided herein for purposes of illustration only and are not intended to be limiting unless otherwise specified.

Preparation of Methylprednisolone Acetate Microparticles With a Poly(d,1-lactide) Excipient A 0.5 g amount of 6α-methylprednisolone acetate, MPA, and 1.5 g of poly(DL-lactide) [DL-PLA] were placed in a mixed solvent comprising 3.0 g of acetone and 35.0 g of methylene chloride. The mixture was stirred with a magnetic stir bar until dissolution was complete. Meanwhile, a 1000 mL resin kettle containing 200 g of 2.5 wt % of aqueous poly(vinyl alcohol) [PVA] in an ice bath was cooled. The resin kettle was equipped with a glass stir shaft having a 2.5-in Teflon impeller which is rotated by a Fisher "Stedi-Speed" stir motor. The PVA solution was given time to cool to about 0° C. before microencapsulation was initiated.

After the PVA had cooled sufficiently, the stir rate was set at 1500 rpm and the organic phase, i.e., the solution of DL-PLA and MPA, was added to the aqueous PVA. After 2 to 3 min of stirring at 1500 rpm, the stir rate was reduced to 900 rpm and the emulsion was allowed to stabilize for 20 min. Next, the pressure in the kettle was reduced to 600 torr to evaporate the organic solvents. The pressure was monitored by a mercury manometer and was adjusted with a bleed valve.

After 30 min of solvent evaporation, a small aliquot of the solution was placed in a 200 mL centrifuge bottle, the aliquot was centrifuged for 1.5 min at about 30G, the PVA supernatant was decanted and the microparticle pellets were resuspended in about 5 mL of de-ionized water. If the microparticles resuspended easily with no agglomeration, the above centrifugation procedure was repeated for the entire batch. After the microparticle pellets from the entire batch were resuspended, the microparticles were transferred to 3000 mL of deionized water while being stirred with a stainless-steel impeller. Stirring of the microcapsules was continued for 1 h. to harden them. The microcapsules were collected either by centrifugation or by vacuum filtration, and then dried overnight in a vacuum chamber maintained at room temperature. The final product was a dry, free-flowing powder.

Table 1 below shows the results obtained with several batches conducted according to the procedure described above.

TABLE I

| Batch | Excipient, g | MPA, g | Methylene Chloride, g | Acetone, g | Aqueous Continuous Phase, g | Stir Rate, rpm | Yield, % of theoretical |
|---|---|---|---|---|---|---|---|
| 1-1 | 1.50$^a$ | 0.50 | 35.0 | 3.0 | 400$^b$ | 600, 430 | 72.5 |
| 1-2 | 1.50$^a$ | 0.50 | 35.0 | 3.0 | 300$^b$ | 600, 400 | 65.5 |
| 1-3 | 0.75$^a$ | 0.25 | 17.5 | 1.5 | 100$^b$ | 1200, 900 | 70.0 |
| 1-4 | 1.50$^c$ | 0.50 | 30.0 | 3.0 | 200$^d$ | 900, 600 | 69.0 |
| 1-5 | 1.50$^e$ | 0.50 | 35.0 | 3.0 | 200$^d$ | 1500, 900 | 62.5 |
| 1-6 | 1.50$^e$ | 0.50 | 35.0 | 3.0 | 200$^d$ | 1500, 900 | 76.5 |

$^a$Polymer Batch 9052-142, inherent viscosity of 0.89 dl/g measured in chloroform at 30° C.
$^b$5 wt % of aqueous PVA
$^c$Polymer Batch 8441-10, inherent viscosity of 0.59 dl/g measured in chloroform at 30° C.
$^d$2.5 wt % of aqueous PVA
$^e$Polymer Batch A656-5, inherent viscosity of 1.02 dl/g measured in chloroform at 30° C.

The initial microencapsulation experiments shown in Table I above were conducted at room temperature. Observation of the microparticle product obtained showed that crystals of the drug had formed on the surface of the microparticles. Moreover, the encapsulation efficiency was low. These observations suggested that the drug was diffusing out of the embryonic microparticles into the aqueous continuous-phase processing medium. In order to resolve this problem the temperature of the micro-encapsulation process was reduced to 0° C., the organic solvent phase to aqueous-phase ratio was increased and the PVA concentration in the aqueous continuous phase was reduced. Batch numbers 1-4 to 1-6 reflect these changes wherein the original 400 g of 5 wt % aqueous PVA in batch 1-1 was replaced with 200 g of 5 wt % aqueous PVA for the preparation of 2-g batches of microparticles. Observations of the microparticle products of batches 1-4 to 1-5 showed no encapsulated drug on the surface of the microparticles. Most likely the reduced temperature, the PVA concentration and the reduced quantity of aqueous phase resulted in a decreased amount of the drug being dissolved in the continuous aqueous phase.

Characterization of Methylprednisolone Acetate Microparticles

The core loading of methylprednisolone acetate in microparticles can be determined by the following dissolution-spectrophotometric technique.

Milligram quantities of microparticles are dissolved in methylene chloride and the absorbance of the solution is measured at 243 nm. The following equation is applicable in calculating the MPA concentration while eliminating the DL-PLA contribution to the absorbance.

$$C_1 = \frac{A_3 - E_2 C_3 - I}{(E_1 - E_2)}$$

wherein A is the absorbance, C is concentration in units of g/dL, E is the extinction coefficient in units of dL/g.cm and I is the sum of the Beer's Law plot intercepts. The numerical subscripts refer to (1) methylprednisolone acetate, (2) DL-PLA and (3) microparticles. The Beer's Law plot intercept for a sample of 6α-methylprednisolone acetate was 0.0014 while the $E^{1\%}$ at 243 nm in dL/g.cm is 356.87. Three samples of DL-PLA gave Beer's Law plot intercepts of +0.0017, +0.0046 and −0.0080 with $E^{1\%}$ values at 243 nm (dl/g.cm) of 0.577, 0.607 and 0.988 respectively. Table II shows the core loadings and encapsulation efficiencies for samples of methylprednisolone acetate microparticles.

TABLE II

| Batch | Core Loading[a], wt % | Encapsulation efficiency, % of theoretical |
|---|---|---|
| 1-1 | 14.5 | 57.8 |
| 1-2 | 9.8 | 39.0 |
| 1-3 | 16.8 | 67.0 |
| 1-4 | 16.4 | 64.0 |
| 1-5 | 17.4 | 69.6 |
| 1-6 | 15.4 | 61.8 |
| 1-7[b] | 15.5 | — |

[a]Composite of Batches 1-5 (1.1 g) and 1-6 (0.4 g).
[b]The theoretical core loading for all batches was 25 wt %.

Measurement of In Vitro Release of Methylprednisolone From Microparticles

The in vitro release of methylprednisolone acetate from microparticles into a receiving fluid comprising 50 wt % of aqueous ethanol maintained at 37° C. was measured. The following protocol was utilized for the IN VITRO model.

Triplicate samples of 20 mg of microparticles were weighed and each sample was placed in an 8-oz bottle containing 150 mL of 50 wt % aqueous ethanol. Methylprednisolone acetate has a saturation solubility greater than 3 ng/ml in 50 wt % of aqueous ethanol and the above sampling procedure meets the standard requirement for infinite-sink conditions, i.e., less than 10% of the saturation solubility of the drug. Next, the bottles were sealed with a thin sheet of Teflon and a screw cap to prevent evaporation. The bottles were then placed in an Eberbach shaker bath oscillating at 120 cycles/min and maintained at 37° C. The amount of drug released from the microparticles as a function of time was measured by determining the absorbance of the aqueous ethanol receiving fluid at 247 nm and by using the following equation based on Beer's Law.

$Absorbance_{247 nm} = 0.03609 C + 0.0076$ wherein C is the concentration of methylprednisolone acetate in g/ml.

The Figure shows the IN VITRO release profiles of samples of the five batches of methylprednisolone containing microparticles identified as 1-1(3), 1-2(4), 1-3(5), 1-5(6) and 1-6(7) in Table II. The Figure also shows the release profiles of two samples of unencapsulated methylprednisolone acetate wherein profile 1 is of a sample of methylprednisolone under the tradename of Depo-Medrol and profile 2 is of a sample of methylprednisolone obtained from the Upjohn Company. The dissolution of Depo-Medrol in 50 wt % aqueous ethanol was complete in 5 min compared to 30 min for the methylprednisolone sample obtained from Upjohn. This difference can be explained by the fact that the crystals of Depo-Medrol are much smaller than the crystalline methylprednisolone product obtained from Upjohn. The profiles clearly show the substantially slower rate of release of methylprednisolone from the various batches of microparticles. The microparticles of batch 1-1 (profile 3) show a slower rate of release of methylprednisolone acetate than the microparticles of batch 1-2 (profile 4) because of the particle size difference of about 20 μm average diameter for batch 1-1 as opposed to about 10 μm average diameter for batch 1-2. The core loadings of these two batches are similar. Thus, as one would expect, faster release rates are found for the smaller microparticles because of their larger surface area.

In Vivo Studies Involving Methylprednisolone Containing Microparticles

The following is the results obtained from a study to evaluate the potential of employing microparticle formulations for the local delivery of corticosteroids to arthritic joints. The IN VIVO studies were performed (1) to determine what size microparticles will remain in the arthritic joint, (2) to determine if the microparticles will irritate the joint, and (3) to demonstrate that the microparticles will efficaciously deliver drug for periods greater than one month in a rabbit model.

A. Experiment Design

Twenty-six rabbits from the Myrtle rabbitry were used for the in vivo studies. They were divided into five experimental groups. Groups A through D each consisted of five rabbits while Group E contained six rabbits.

1. Group A

Sterile MPA microparticles (Batch 1-7 from Table II) were injected into the shaved right knee of each rabbit in Group A using physiological saline as the injection vehicle. Each knee received 20 mg of microencapsulated MPA. The purpose of this control group was to demonstrate that MPA microcapsules did not induce arthritis in normal joints. The rabbits were therefore examined twice a week for clinical evidence of arthritis.

2 Group B

Each of the rabbits in Group B were induced with arthritis by the following protocol:

An emulsion of 10 mg/mL of bovine serum albumin, BSA, in pyrogen free saline, PFS, and an equal volume of complete Freud's adjuvant was prepared and 2 mg was injected intramuscularly into the thigh of each rabbit. Three weeks later, 0.25 mg of BSA in PFS was injected intradermally into the shaved back of each rabbit to assess skin response. The presence of anti-BSA antibodies was determined by drawing 5 mL of blood from the ear vein of the immunized rabbits. The blood was incubated at 37° C. for 2 h and then refrigerated. Each sample was centrifuged at 3000 rpm for 10 min. The serum was then separated and centrifuged at 20,000 rpm for 30 min. Agar Outcherlony plates were prepared and the central holes were filled with 0.5 mL of a 1 mg/mL BSA solution and 0.5 mL of a 10 mg/mL BSA solution. Peripheral holes were filled with 0.5 mL of undiluted rabbit serum and with dilutions of 1:5, 1:10, 1:20, 1:50, and 1:100 in Tris buffer-saline, TBS. Each of the plates were read at 8, 12 and 24 h and the last line of precipitation was considered as the positive response. Arthritis was induced in each rabbit by injecting intra-articularly 1 mg of BSA in PFS into the right shaved knee once a week for three weeks. The opposite knee was injected with equal amounts of PFS.

Two weeks after the last intra-articular injection of BSA the Group B rabbits were injected intra-articularly with sterile microparticles containing 20 mg of MPA using physiological saline as the injection vehicle. This particular batch of microparticles contained a core loading of 14.9% MPA, and had a particle size range of 2 to 40 µm in diameter with an average particle size of 20 µm. The polymeric excipient was d,l-polylactide and the microparticles were sterilized with 2 megarads of radiation. Each rabbit was examined one to three times a week for three months, then one rabbit from the group was sacrificed every two weeks. Both knees were examined grossly and the synovium was examined microscopically.

3. Group C

Each of the Group C rabbits was induced with arthritis by the protocol used for rabbits in Group B. Two weeks after the last intra-articular injection of BSA, these rabbits were injected intra-articularly with 20 mg of unencapsulated MPA (Depo-Medrol), using the injection vehicle supplied with the commercial Depo-Medrol product. Each rabbit was then examined and sacrificed by the protocol used for the Group B rabbits.

4. Group D

The rabbits in Group D were also induced with arthritis by the previously mentioned protocol. However, they received no treatment. These rabbits were also examined and sacrificed by the same protocol used for Groups B and C.

5. Group E

The six rabbits in Group E were injected intra-articularly with DL-PLA microspheres, empty microcapsules containing no drug. This control group received the same polymer that was used to prepare the MPA microcapsules injected in Group A and Group B rabbits.

B. Results of IN VIVO Studies

The 15 rabbits in Groups B, C and D were immunized with BSA in PFS and complete Freund's Adjuvant. All of the rabbits had a positive arthritis reaction in the area injected with 0.25 mg of BSA intra-dermally. Twelve rabbits showed precipitation lines at the 1:5 dilutions on the Outcherlony plates for anti-BSA antibodies. The other three rabbits showed no lines of precipitation. However, all 15 rabbits developed arthritis following injection of BSA antigen intra-articularly.

All of the rabbits in Group A (injected with sterile MPA microcapsules at a total dose of 20 mg of MPA) had no gross evidence of arthritis on premortem examinations and no synovitis was seen on open knee examination. Micro-scopic examinations showed that the MPA microcapsules were surrounded by inflamatory cells with the outer layers of microcapsules showing less cellular infiltrate. The synovium itself appeared normal.

The arthritic rabbits in Group B (injected with sterile MPA microcapsules at a total dose of 20 mg of MPA) and those in Group C (injected with 20 mg of unencapsulated MPA) showed little difference in the periodic clinical examinations. However, as the knees were opened, the proliferation of synovium and overall inflammation was more marked in the Group C rabbits, particularly after 14 weeks post-corticosteroid injection. Histologically, there were significant differences between the synovium of rabbits in Group C which had exuberant proliferations of synovium and cellular infiltrates and the almost normal looking synovium of rabbits in Group B.

The arthritic rabbits in Group D (no treatment) had persistent inflammation. This inflammation included joint swelling, synovial proliferation, and cellular infiltrates.

Group E rabbits (injected with sterile DL-PLA microspheres) showed no gross evidence of inflammation during the six weeks of observation. Microscopic examinations showed cellular infiltration around the microspheres that was more pronounced than the infiltration seen in Group A rabbits. However, the cellular infiltrate seemed to be more intense at 2 weeks post injection than at 6 weeks. The synovium itself appeared normal.

The findings of this study indicate that MPA microcapsules ranging in diameter from 2 to 40 µm will remain in arthritic joints. In addition, the presence of these microcapsules in the absence of MPA does not appear to induce arthritis. Even though some inflammation is seen, it appears to be more pronounced immediately following injection and to decrease with time. Furthermore, it appears that MPA microcapsules are more effective in reducing the inflammation and cellular infiltration in arthritic joints in the rabbit model than are injections of Depo-Medrol.

Having now fully described the invention, it will be apparent to one of ordinary skill in the art that many changes and modifications can be made thereto without departing from the spirit or scope of the invention as set forth herein.

What is claimed as new and is intended to be secured by Letters Patent is:

1. An anti-inflammatory agent containing microparticle composition prepared by a process, comprising:
   (a) dissolving or dispersing an anti-inflammatory agent selected from the group consisting of a prednisolone, a triamcinolone, a dexamethasone and a β-methasone in a solvent selected from the group consisting of acetone, a halogenated hydrocarbon, an aromatic hydrocarbon, a halogenated aromatic hydrocarbon, a cyclic ether, an alcohol and water and dissolving a biocompatible and biodegradable wall forming material in said solvent;

(b) dispersing said solvent containing said anti-inflammatory agent and wall forming material in a continuous phase processing medium of water, toluene, xylene, a synthetic oil or a natural oil;

(c) evaporating a portion of said solvent from said dispersion of step (b), thereby forming microparticles containing said anti-inflammatory agent in the suspension; and (d) extracting the remainder of the solvent from said microparticles.

2. The composition of claim 1, wherein the polymeric matrix material of said microparticles is poly-d,1-lactic acid, polyglycolic acid, copolymers of mixed d,1-lactic acid and glycolic acid, copolyoxalates, polycaprolactone, or poly (lactic acid-caprolactone).

3. The composition of claim 1, wherein said microparticles are loaded with 1 to 75 wt. % of said anti-inflammatory agent based on said polymeric matrix.

4. The composition of claim 1, wherein said microparticles range in size from 1 to 200 microns.

5. The composition of claim 1, wherein said microparticles are formulated in a liquid injectable vehicle.

6. A method of treating inflammation comprising:
administering microparticles of claim 1 containing a pharmaceutically effective amount of an anti-inflammatory compound in a biocompatible and biodegradable matrix material to a subject.

7. The method of claim 6, wherein said microparticles are formed of a matrix of polymeric d,1-lactic acid, glycolic acid, copolymers thereof, copolyoxalates, polycaprolactone or poly (lactic acid-caprolactone).

8. The method of claim 6, wherein from microgram to milligram quantities of said corticosteroid are administered per day to a subject.

9. The method of claim 6, wherein said microparticles are administered by injection into the area of the inflammed joints of an affected subject.

10. The method of claim 6, wherein said injectable microparticles are formulated as microparticles in a liquid vehicle.

11. The method of claim 10, wherein said liquid vehicle is physiological saline solution.

12. The method of claim 6, wherein said micro-particles are administered by intra-muscular injection.

* * * * *